United States Patent [19]

Hartmann et al.

[11] Patent Number: 5,727,942
[45] Date of Patent: Mar. 17, 1998

[54] JAW IMPLANT ARRANGEMENT WITH AN IMPLANT SHAFT AND AN INSERTION TOOL

[76] Inventors: Alexander Hartmann, Wintererstr. 57, D 79104 Freiburg; Wilfried Schilli, Horbener Str. 27, D-79100 Freiburg, both of Germany

[21] Appl. No.: 687,568

[22] PCT Filed: Dec. 14, 1995

[86] PCT No.: PCT/EP95/04942

§ 371 Date: Aug. 9, 1996

§ 102(e) Date: Aug. 9, 1996

[87] PCT Pub. No.: WO96/18355

PCT Pub. Date: Jun. 20, 1996

[30] Foreign Application Priority Data

Dec. 14, 1994 [DE] Germany .................. 9420038 U

[51] Int. Cl.⁶ ...................................... A61C 8/00
[52] U.S. Cl. ................. 433/173; 433/141; 433/163; 433/174
[58] Field of Search .................... 433/174, 172, 433/173, 175, 141, 163

[56] References Cited

U.S. PATENT DOCUMENTS

| | | | |
|---|---|---|---|
| 4,850,870 | 7/1989 | Lazzara et al. | 433/174 |
| 4,872,839 | 10/1989 | Brajnovic | 433/173 |
| 5,087,200 | 2/1992 | Brajnovic | 433/174 |
| 5,135,395 | 8/1992 | Marlin | 433/174 |
| 5,209,666 | 5/1993 | Balfour et al. | 433/173 |
| 5,290,171 | 3/1994 | Daftary et al. | 433/141 |
| 5,350,300 | 9/1994 | Gallais | 433/141 |
| 5,350,302 | 9/1994 | Marlin | 433/174 |
| 5,362,236 | 11/1994 | Branemark | 433/174 |
| 5,407,359 | 4/1995 | Balfour et al. | 433/173 |

FOREIGN PATENT DOCUMENTS

| | | |
|---|---|---|
| 320024 | 6/1989 | European Pat. Off. |
| 473262 | 3/1992 | European Pat. Off. |
| 2703903 | 10/1994 | France. |
| 2834890 | 5/1979 | Germany. |
| 618870 | 8/1980 | Switzerland. |
| 679117 | 12/1991 | Switzerland. |
| 684384 | 9/1994 | Switzerland. |

OTHER PUBLICATIONS

Translation of the Abstract of CH 618,879.
Translation of the Abstract of CH679,117.
Translation of the Abstract of CH684,384.

*Primary Examiner*—John J. Wilson
*Attorney, Agent, or Firm*—Quarles & Brady

[57] ABSTRACT

An implant arrangement for securing a denture to a jawbone includes an implant shaft which is provided at its upper end with a threaded bore whose central axis is inclined relative to the central axis of the implant shaft. The implant shaft can therefore be inserted into the jawbone such the implant shaft is inclined relative to the denture crown axis while the crown axis of the denture itself remains in the desired position. The angled implant can be inserted in a rotationally symmetrical manner without requiring additional space, even in narrow tooth gaps, by means of a special screwed-on insertion instrument.

10 Claims, 1 Drawing Sheet

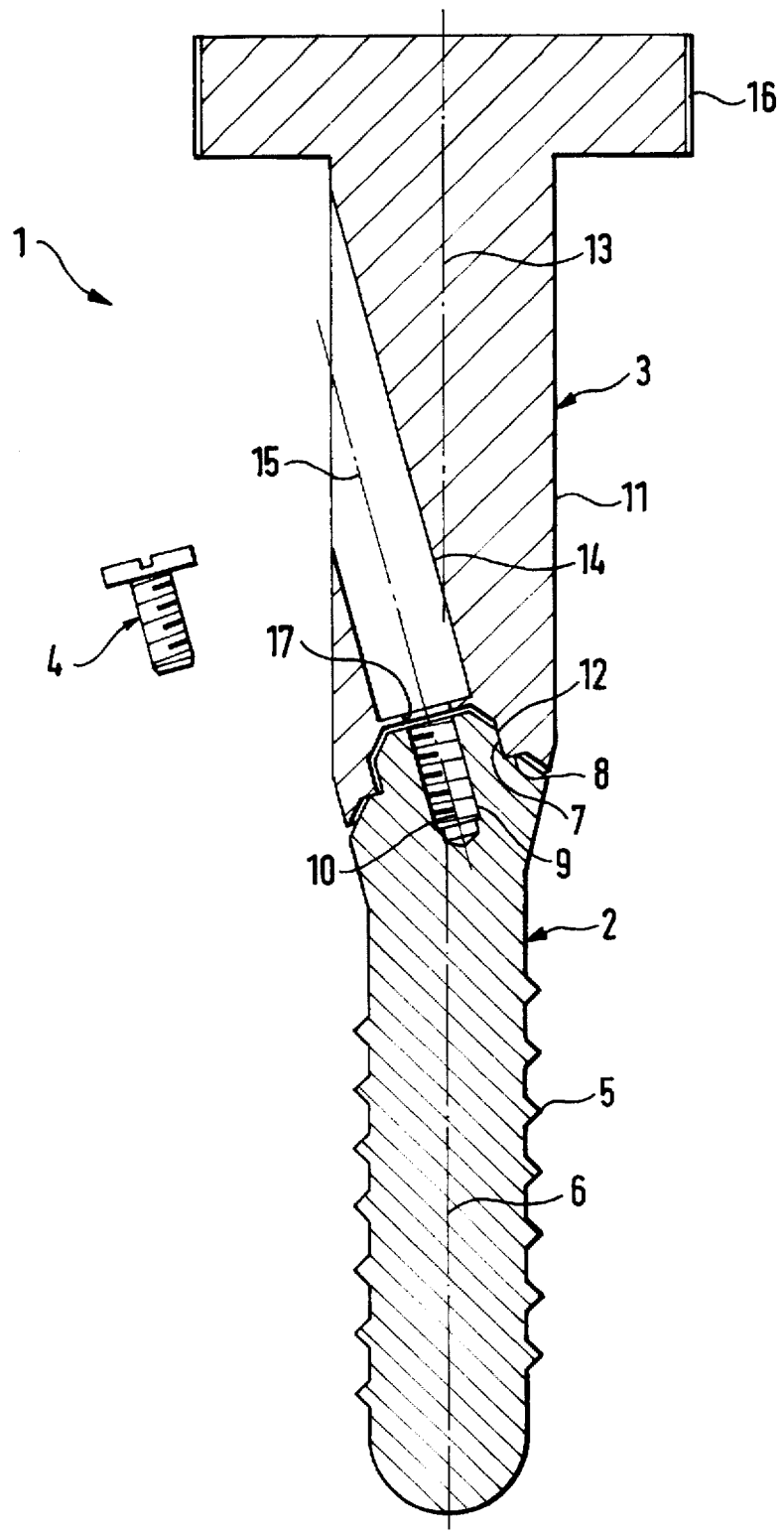

JAW IMPLANT ARRANGEMENT WITH AN IMPLANT SHAFT AND AN INSERTION TOOL

In dental implantology often cylindrical, rotationally symmetric bodies having a screw thread are used when employing artificial implants for anchoring fixed or removable dentures. The CH 684 384 A5 discloses an implant arrangement with an implant shaft being formed as a cylindrical, rotationally symmetric body of this kind for insertion into a jawbone. A threaded blind hole having a central axis coincident with the central axis of the implant shaft is provided at the end of the implant shaft away from the jawbone. A holding device having a central axis coincident with the central axis of the threaded blind bore may be screwed into the same. An artificial denture having a crown axis coincident with the central axis of the holding device and of the threaded blind bore can be mounted to the holding device.

The positioning of the implant, however, depends on the amount of bone available at the upper or lower jaw, resp. This often results in divergencies between the implant axis, the central axis of the implant shaft and the prosthetically required crown axis. In the above implant apparatus this axial divergence can be compensated by individual accessory units mounted on the straight implant shaft.

The accessory units increase the complexity of the implant as a whole and the costs.

It is therefore the object of the present invention to provide an implant arrangement which is suitable for securing a denture at a jawbone in a simple manner and at a low price even if the available amount of bone is insufficient.

This object is achieved by an implant arrangement for securing a denture at a jawbone having the features of claim 1.

The screwed-on insertion tool renders the angled implant arrangement rotationally symmetric and can be inserted without requiring additional space even in narrow tooth gaps.

Further developments of the implant arrangement are defined in the subclaims.

Further features and advantages of the invention will be apparent from the following description with reference to the FIGURE.

The FIGURE shows the implant arrangement according to an embodiment of the present invention.

The implant arrangement 1 according to one embodiment of the invention comprises an implant shaft 2, an insertion tool 3 and a bolt 4.

The implant shaft 2 forming the implant proper when inserted into the (not shown) jawbone has an external screw thread 5. The central axis 6 of the implant shaft 2 is coaxial with the external screw thread 5. A head having a projection 7 is formed at the end of the implant shaft 2 which faces away from the jawbone when the implant shaft is inserted. The projection 7 is shaped as an octagon nut or as an octagon screw head and projects from an upper face 8 of the head. A shoulder is formed by the projection 7 and the upper face 8. The axis perpendicular to the upper face 8 is inclined with respect to the central axis 6 of the implant shaft 2 by a predetermined angle, for example by 20°. The central axis of the projection 7 is as well inclined with respect to the central axis 6 of the implant shaft 2 by the predetermined angle. A threaded blind bore 9 is formed in the projection 7. The central axis 10 of the threaded blind bore 9 is coaxial with the central axis of the projection 7.

The predetermined angle between the central axis 6 of the implant shaft 2 and the central axis 10 of the threaded blind bore 9 or the central axis of the projection 7, resp., corresponds to the suitable insertion angle of the implant into the jawbone so that the central axis 10 of the threaded blind bore 9 or the central axis of the projection 7, resp., coincides with the crown axis of the (not shown) denture to be secured, even if the available amount of bone is insufficient.

The insertion tool 3 of the implant arrangement 1 has a substantially cylindrical shaft 11. One end of the insertion tool 3 has a recess 12 with an octagon socket so that the recess 12 snugly fits onto the projection 7. The central axis of the recess 12 is inclined with respect to the central axis 13 of the cylindrical shaft of the insertion tool by the same angle as the central axis 10 of the threaded blind bore 9 of the implant shaft 2.

A first bore 12 extends from the periphery of the cylindrical shaft 11 up to a point close to the recess 12. A central axis 15 of the first bore 14 is inclined relative to the central axis 13 of the cylindrical shaft 11 of the insertion tool 3 by the same angle as the central axis 10 of the threaded blind bore 9 of the implant shaft 2.

A handle 16 is provided at the end of the insertion tool 3 opposite to the end having the recess 12. In the portion of the first bore 14 adjacent to the bottom of the recess 12 a second bore 14 is provided to form a hole 17 with a diameter which is smaller than the general diameter of the first bore 14.

The bolt 4 of the implant arrangement 1 is dimensioned to allow the bolt 4 to be screwed into the threaded blind bore 9. The inner diameter of the hole 17 is sized to let the threaded shaft of the bolt 4 pass through the hole 17. The head diameter of the bolt 4 has a size so that it does not pass through the hole 17 of the first bore 14.

The implant arrangement is used as follows.

First a bore hole is bored into the jawbone at the position where the denture is to be secured. The orientation of the bore hole depends On the available amount of bone in the upper or lower jaw. The diameter of the bore is selected to be slightly smaller than the diameter of the implant shaft 2. An internal screw thread which is slightly smaller than the external screw thread 5 of the implant shaft 2 is cut into the bore.

The depth of the bore hole is made to be larger than the length of the implant shaft 2 by one turn of the thread. The insertion tool 3 is placed onto the implant shaft 2 so that the central axis 6 of the implant shaft 2 coincides with the central axis 13 of the insertion tool 3. Thus, the central axis 10 of the threaded blind bore 9 is coaxial with the central axis 15 of the first bore 14. The bolt 4 is inserted through the first bore 14 into the insertion tool, passed through the hole 17 and screwed into the threaded blind bore 9 so that the insertion tool 3 is fixed to the implant shaft 2.

Thereupon the implant shaft 2 is screwed into the bore hole bored into the jawbone by rotating the insertion tool 3. The final rotational position of the implant shaft 2 is selected so that the visible first bore 14 is oriented in the direction which coincides with the crown axis of the denture to be mounted. It is therefore important that the bore hole in the jawbone is about 1 mm deeper than the length of the implant shaft, whereby any unsuitable rotational position can be corrected by further screwing-in when using a thread pitch of 1 mm. Thereafter the bolt 4 is unscrewed so that the insertion tool 3 can be removed from the implant shaft 2.

The crown axis of the denture placed onto the implant shaft is oriented in the desired direction, i.e. the axial direction of the replaced tooth. The implant shaft 2, however, is oriented in the jawbone in a direction which is predetermined by the available amount of bone material. Thus, the central axis of the implant shaft 2 not necessarily forms an extension of the crown axis.

We claim:

1. Implant arrangement for securing a denture to a jawbone, said implant arrangement comprising:

implant shaft means having a central axis, a first end for insertion into the jawbone and a second end, securing means including a threaded bore formed at said second end for securing said denture thereto, said threaded bore being inclined with a predetermined angle relative to said central axis, and insertion tool means for inserting said implant shaft means into the jawbone, said insertion tool means having a central axis and a first end removably connected to said implant shaft for rotationally inserting said implant shaft into said jawbone, connection means formed at said first end of said insertion tool means with an inclination relative to said central axis of said insertion tool means corresponding to said predetermined angle, said connecting means removably interfacing said insertion tool means and said implant shaft, wherein said central axis of said insertion tool means is coaxial with said central axis of said implant shaft.

2. The implant arrangement of claim 1, wherein said implant shaft means comprises an external screw thread.

3. The implant arrangement of claim 1, wherein said securing means comprises a head with a projection formed as an octagon head, said threaded bore extending through said octagon head.

4. The implant arrangement of claim 3, wherein said first end defines a recess with an octagon socket for insertion of said octagon head into said octagon socket.

5. The implant arrangement of claim 1, wherein said securing means comprises a peripheral shoulder for receiving a corresponding face formed at said first end of said insertion tool means.

6. The implant arrangement of claim 1, wherein said insertion tool means defines a first bore extending from a periphery of said insertion tool means towards said first end with an inclination relative to said central axis of said insertion tool means, said inclination corresponding to the inclination of said threaded bore relative to the central axis of said implant shaft means, and wherein said insertion tool means defines a second bore having a diameter which is smaller than the diameter of said first bore and communicating said first bore with said first end of said insertion tool means.

7. The implant arrangement of claim 1, comprising a handle formed at an end of said insertion tool means opposite to said first end for operating said insertion tool means.

8. Implant arrangement for securing a denture to a jawbone, said implant arrangement comprising:

substantially cylindrical implant shaft means having a central axis and a predetermined diameter, a first end for insertion into the jawbone and a second end, securing means including a threaded bore formed at said second end for securing said denture thereto, said threaded bore being inclined with a predetermined angle relative to said central axis and having a contour with a maximum distance from said central axis which is smaller than said predetermined diameter, insertion tool means for inserting said implant shaft means into the jawbone, said insertion tool means having a central axis and a first end removably connected to said implant shaft for rotationally inserting said implant shaft into said jawbone, connection means formed at said first end with an inclination relative to said central axis corresponding to said predetermined angle removably interfacing said insertion tool means and said implant shaft, wherein said central axis of said insertion tool means is coaxial with said central axis of said implant shaft means.

9. The implant arrangement of claim 8, wherein said insertion tool means has a substantially cylindrical portion formed adjacent to said first end, said substantially cylindrical portion having a diameter corresponding to said predetermined diameter of said implant shaft means or being slightly greater than said predetermined diameter.

10. Implant arrangement for securing a denture to a jawbone, said implant arrangement comprising:

implant shaft means having a central axis, a first end for insertion into the jawbone and a second end, securing means including a threaded bore formed at said second end for securing said denture thereto, said threaded bore being inclined with a predetermined angle relative to said central axis, and insertion tool means for inserting said implant shaft means into the jawbone, said insertion tool means having a central axis and a first end removably connected to said implant shaft for rotationally inserting said implant shaft into said jawbone, connection means formed at said first end of said insertion tool means with an inclination relative to said central axis of said insertion tool means corresponding to said predetermined angle, said connecting means for connecting said insertion tool means to said implant shaft, wherein said central axis of said insertion tool means is coaxial with said central axis of said implant shaft, wherein said insertion tool means defines a first bore extending from a periphery of said insertion tool means towards said first end with an inclination relative to said central axis of said insertion tool means, said inclination corresponding to the inclination of said threaded bore relative to the central axis of said implant shaft means, wherein said insertion tool means defines a second bore having a diameter which is smaller than the diameter of said first bore and communicating said first bore with said first end, and a bolt extending through said second bore into said threaded bore for securing said insertion tool means to said implant shaft means.

* * * * *